US008501988B2

(12) United States Patent
Miralles et al.

(10) Patent No.: US 8,501,988 B2
(45) Date of Patent: Aug. 6, 2013

(54) SYNTHESIS AND APPLICATIONS OF AMINO CARBOXYLATES

(75) Inventors: Altony J. Miralles, Woodbury, MN (US); Carter M. Silvernail, St. Louis Park, MN (US)

(73) Assignee: Ecolab USA Inc., St. Paul, MN (US)

( * ) Notice: Subject to any disclaimer, the term of this patent is extended or adjusted under 35 U.S.C. 154(b) by 771 days.

(21) Appl. No.: 12/401,715

(22) Filed: Mar. 11, 2009

(65) Prior Publication Data
US 2009/0264677 A1 Oct. 22, 2009

Related U.S. Application Data

(60) Provisional application No. 61/045,805, filed on Apr. 17, 2008.

(51) Int. Cl.
C07C 229/04 (2006.01)

(52) U.S. Cl.
USPC .......................................... 562/571

(58) Field of Classification Search
None
See application file for complete search history.

(56) References Cited

U.S. PATENT DOCUMENTS

| | | | |
|---|---|---|---|
| 2,500,019 A | 10/1946 | Bersworth | |
| 3,642,887 A | 2/1972 | Jackisch | |
| 5,362,412 A | 11/1994 | Hartman et al. | |
| 5,543,566 A | 8/1996 | Takahashi et al. | |
| 5,668,147 A * | 9/1997 | Nakano et al. ................ | 514/312 |
| 5,851,970 A | 12/1998 | Saito et al. | |
| 6,013,612 A | 1/2000 | Saito et al. | |
| 6,190,451 B1 | 2/2001 | Soya et al. | |
| 6,194,373 B1 | 2/2001 | Saito et al. | |
| 6,221,834 B1 | 4/2001 | Yamamoto et al. | |
| 6,334,944 B1 | 1/2002 | Nambu et al. | |
| 6,426,229 B1 | 7/2002 | Yamamoto et al. | |
| 6,451,757 B2 | 9/2002 | Yamamoto et al. | |
| 6,451,881 B1 | 9/2002 | Vickers, Jr. et al. | |
| 6,527,931 B2 | 3/2003 | Nambu et al. | |
| 2001/0007042 A1 | 7/2001 | Van Doorn et al. | |
| 2003/0195129 A1 | 10/2003 | Ishikawa et al. | |
| 2006/0111265 A1 | 5/2006 | Rypkema et al. | |
| 2006/0281661 A1 | 12/2006 | Ishikawa et al. | |
| 2007/0134284 A1 | 6/2007 | Parker | |

FOREIGN PATENT DOCUMENTS

| | | | |
|---|---|---|---|
| EP | 1 004 571 B1 | 5/2000 | |
| EP | 1762563 | 3/2007 | ...................... 227/8 |
| EP | 1 795 273 A1 | 6/2007 | |
| WO | WO 01/83657 A2 | 11/2001 | |

OTHER PUBLICATIONS

Choquesillo-Lazarte, Duane, et al., *Metal Chelates of N-(2-pyridylmethyl)iminodiacetate(2-) ion (pmda)*, Polyhedron 21, pp. 1485-1495, 2002.
Chu, Qian, et al., *Structure Modulation of Metal-Organic Frameworks via Reaction pH*, Polyhedron 27(2), pp. 812-820, Feb. 6, 2008.
Haggman, L. et al., *The Influence of Short Strong Hydrogen Bonding on the Structure and the Physiochemical Properties of Alkyl-N-iminodiacetic Acids in Solid State and Aqueous Systems*, Journal of the American Chemical Society, 125(2) pp. 3631-3641 (2003).
Potgieter, Hein, et al., *Identification of different (Co) III apda complexes*, Polyhedron, 24(15), pp. 1968-1974, (2005).
Rojas-Gonzales, Perla X., et al., *Synthesis, Crystal Structure and Properties of N-tert-butyliminodiacetic acid* Polyhedron 22, pp. 1027-1037, (2003).
Sanchez-Moreno, M.J., et al., *Ring-ring or nitro-ring π, πinteractions in N-(p-nitrobenzyl) iminodiacetic acid*, Polyhedron 22(8), pp. 1039-1049, (2003).
Xu, Yanqing, et al., *1D Tube, 2D Layer, and 3D Framework Derived from a New Series of Metal (II)-5-Aminodiacetic Isophthalate Coordination Polymers*, Crystal Growth & Design vol. 6 No. 5 pp. 1168-1174, (2006).
Yong, Guo-Ping, et al., *Synthesis, Structural Characterization and Properties of Copper (II) and Zinc(II) Coordination Polymers with a New Bridging Chelating Ligand*, Eur. J. Inorg. Chem. vol. 21, pp. 4317-4323, (2004).

* cited by examiner

*Primary Examiner* — Rosalynd Keys
(74) *Attorney, Agent, or Firm* — Andrew D. Sorensen; Amy J. Hoffman

(57) ABSTRACT

A method of synthesizing carboxylated amines is disclosed. The method comprises reacting a mixture of a potassium salt of either a primary or secondary amine with a potassium salt of a halogenated carboxylic acid wherein the halogenated carboxylic acid is selected from the group consisting of brominated, chlorinated, or iodinated carboxylic acid in the presence of potassium hydroxide, and optionally in heating the reacting mixture; precipitating the potassium salt by optionally chilling the mixture and discarding the precipitate; purifying the carboxylate amine potassium salt from the liquid phase using water soluble alcohol and optionally adding formic acid to obtain the free aminocarboxylic acid and potassium formate. In a preferred embodiment, the halogenated carboxylic acid is chloroacetic acid.

14 Claims, No Drawings

SYNTHESIS AND APPLICATIONS OF AMINO CARBOXYLATES

RELATED APPLICATIONS

This application claims priority under 35 U.S.C. §119(e) to U.S. Provisional Application entitled "Novel Synthesis And Applications Of Amino Carboxylates," Ser. No. 61/045,805, filed on Apr. 17, 2008, which is incorporated herein by reference in its entirety for all purposes.

FIELD OF THE INVENTION

The invention relates to chemical processes and more particularly to a method of synthesizing carboxylated amines. The method provides a synthesis to attach carboxylate functional group to a primary or secondary amine. More particularly, the invention relates to a method of forming carboxylated amines free of nitrilotriacetic acid and substantially free of contaminating salt byproducts. The method yields carboxylated amines with active concentrations of greater than 30% by weight isolated as either a metal salt or free acid.

BACKGROUND

Chelating agents are molecules that form two or more coordinated covalent bonds to a metal ion and are also classified as sequestering agents. The most commonly used chelating agents are those that coordinate to a central metal ion through oxygen, nitrogen, or a combination of oxygen and nitrogen donor atoms yielding the respective inorganic coordination compound. Chelating or sequestering agents typically form water-soluble metal complexes and therefore are very useful in various industrial and commercial applications including pulp and paper manufacturing, metalworking and metal plating, pharmaceuticals, water treatment, textile manufacturing and dyeing, agriculture, cleaning and detergent formulations, and food processing. Chelating or sequestering agents may be used in the aforementioned applications alone or with surfactants, builders or other chelating agents.

A major concern surrounding chelating agents is environmental accumulation as a result of persistence meaning the inability to biodegrade under environmental conditions. For example, ethylenediaminetetracetic acid (EDTA), a preferred chelating agent due to its low cost and high metal binding affinity over a large pH range has been scrutinized because of its environmental persistence. Elevated concentrations of EDTA and other nonbiodegradable chelating agents pose major environmental concerns such as heavy metal remobilization and plant (e.g. algae) growth alteration. As a result, many processes and methods have been reported for the preparation of biodegradable chelating agents.

Current methods have focused on the use of sustainable and/or renewable feedstocks to produce biodegradable chelating agents. However, a commonly utilized process for the industrial preparation of many chelating agents involves the use of cyanide, formaldehyde and sodium hydroxide resulting in nitrilotriacetic acid (NTA) contamination. While NTA is biodegradable, it is not preferred from the point of environmental health because it has been reported that NTA has teratogenicity and nitrilotriacetic acid-iron complex has carcinogenicity. Among other conventional carboxylated amines, those that are excellent in chelating performance, but are low in biodegradability have the difficulty that they accumulate as injurious heavy metals in the environment when they are discharged into the environment. Other processes for synthesizing carboxylated amines are disadvantageous due to high salt concentrations; for example, they contain high sodium chloride concentrations that can only be removed through tedious purification steps (i.e. ion exchange).

Accordingly, a need exists for another method for preparing chelating or sequestering agents. Disclosed is a method for synthesizing biodegradable chelating agents free of NTA with miniscule concentration of salt byproducts that minimizes production cost and avoids undesirable byproduct contamination.

SUMMARY

A method of synthesizing carboxylated amines is disclosed. In particular, a method of synthesizing carboxylated amines comprising reacting a mixture of potassium salt of a primary or secondary amine and a potassium salt of a halogenated carboxylic acid, preferably chloroacetic acid, in the presence of potassium hydroxide and heat; chilling the mixture to precipitate the potassium chloride and separating the precipitate from the mixture; adding alcohol to the chilled mixture to purify the carboxylated amine potassium salt. Examples of suitable halogenated carboxylic acids include chloroacetic acid as previously mentioned, bromoacetic acid, iodoacetic acid, chloropropionic acid, bromopropionic acid, and iodopropionic acid. Halogenated carboxylates that are not suitable for the invention are fluorinated carboxylic acids as well as astatined carboxylic acids. One skilled in the art will recognize that the high electronegativity of fluorine will hinder its replacement by nitrogen. Astatine, on the other hand, is radioactive and readily decays.

A method of synthesizing an amino carboxylic acid functionalized molecule is disclosed. The method comprises reacting an amino-functional group containing molecule lacking acidic functional groups with the potassium salt of a halogenated carboxylic acid in the presence of potassium hydroxide and heat; chilling the mixture to precipitate the potassium chloride and separating the precipitate from the mixture; adding alcohol to the chilled mixture to purify the carboxylated amino acid potassium salt.

Disclosed is a synthetic procedure to attach carboxylate functional groups to a primary or secondary amine resulting in an aminocarboxylate. The resulting aminocarboxylates may be isolated in either the free acid or metal salt form. The synthetic method for isolating the free acids of aminocarboxylates consists of first combining an amino acid or a molecule containing an amine functional group in aqueous potassium hydroxide with a halogenated carboxylic acid selected from the group consisting of brominated, chlorinated, or iodinated carboxylic acids in aqueous potassium hydroxide. Next the resultant mixture is heated and an alkaline pH is maintained by the addition of aqueous potassium hydroxide. Once the pH is stabilized without further addition of potassium hydroxide, the reaction mixture is boiled for an additional 10 minutes, cooled and the precipitated potassium chloride is removed by filtration. The filtrate is acidified with formic acid and an equal weight of water-soluble alcohol is added to the filtrate thus causing the resulting potassium formate to solubilize in the water-alcohol layer. The bottom saturated aqueous layer containing the desired aminocarboxylic acid is conveniently separated using a separatory funnel and further purification using alcohol is optional.

A synthetic method for isolating the potassium salts of aminocarboxylates is disclosed. The method comprises combining an amino acid or a molecule containing an amine functional group in aqueous potassium hydroxide with chloroacetic acid, heating the resulting combination and maintaining an alkaline pH by adding aqueous potassium hydroxide. Mixing at elevated temperature once the pH is stabilized. Cooling the reaction mixture and removing the precipitated potassium chloride. Purifying the product by adding alcohol and removing any resulting precipitate of potassium chloride.

The method provided enables the isolation of aminocarboxylates in the form of a free acid or potassium salt. The method of the invention provides an efficient synthetic route to form aminocarboxylates avoiding nitrilotriacetic acid (NTA) impurities. Furthermore, the described synthetic method provides a novel route to aminocarboxylates in which salt byproducts are readily separated from the reaction mixture enabling minimal purification.

A synthetic carboxylated amine is provided that is free of nitrilotriacetic acid.

DETAILED DESCRIPTION

As used herein, the terms amino carboxylic, or amino carboxylate, or carboxylated amine all refer to a molecule containing both amine and carboxyl functional groups bound to the amine group.

As used herein, the terms amine-functional group or amino-functional group are used interchangeably and refer to any molecule having an amine group. By use of the term amine-functional, we refer to any molecule exhibiting an amine or amino group, including but not limited to primary amines and secondary amines.

The term functionalized, as used herein, refers to a molecule having a certain functional group. For example, an amino functionalized molecule refers to a molecule having an amino functional group.

One use of the chemicals produced by this invention is in cleaning products. In particular, molecules having amino and carboxylate functionality serve as excellent chelating agents. Chemicals prepared according to the present invention may be used in any product normally containing a chelating agent. A chemical prepared according to the present invention is a chelant, which also can be referred to as a sequestrant or complexing agent. In particular, chelating agents and, therefore, the product of this invention, are used to control metal ion activity in aqueous systems. Through their use, precipitation of sparingly soluble salts such as calcium and magnesium, with inorganic anions, fatty acids, and anionic surfactants can be avoided. These include but are not limited to scale control in cleaners, water softening, and as a builder in laundry detergents.

It has surprisingly been discovered that molecules having amino and carboxylate functionality, for example, N,N-Diacetic acid functionality, may be synthesized without the concomitant production of contaminating nitrilotriacetic acid and salt byproducts and, as a result, in very high purity.

Amino carboxylates prepared according to the present invention have small amounts of contaminating salts as compared to methods currently known in the art. In a preferred embodiment amino carboxylates prepared according to the invention contain less than about 20 percent contaminating salt. In a more preferred embodiment, the synthetic amino carboxylates prepared according to the invention contain less than about 10 percent contaminating salt, and in a most preferred embodiment the amino carboxylates prepared according to the invention contain less than about 5 percent contaminating salts. This is contrasted to amino carboxylates prepared using sodium chloride rather than the potassium chloride preferred in the present invention. Amino carboxylates prepared using sodium chloride are generally contaminated with at least about 14 percent salt.

Any chemical having an amino-functional group can serve as the starting material in synthesizing an amino carboxylate according to the invention. Examples of such chemicals include, but are not limited to amino acids. As used herein, the term amino acid refers to any naturally occurring amino acid. Examples of naturally occurring standard amino acids include, but are not limited to alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. Naturally occurring nonstandard amino acids include but are not limited to selenocysteine, pyrrolysine, lantionine, 2-aminoisobutyric acid, dysrolanine, gamma-aminobutyric acid, homocysteine, and hydroxyproline.

Yet other examples of chemicals useful as the starting materials for the synthesis of the invention include but are not limited to ethylamine, dimethylaminoethylamine, 1,2-diaminopropane, N,N-dimethylethylenediamine, 2-methoxyethylamine, Amino-2-propanol, 2-(2-aminoethoxy)ethanol, aminobenzoic acid, benzylamine, cyclohexylamine and 2,2',2"-triaminotriethylamine (TAEA).

The conversion of an amine functional group to an aminocarboxylate is well known in the art. As previously stated, common methods for the conversion of an amine to an aminocarboxylate generate NTA and/or high concentrations of metal salts (e.g. NaCl) that are only removed by tedious purification steps. The solubility of potassium chloride significantly decreases with decreasing temperature as opposed to sodium chloride, which exhibits an almost constant solubility over a wide temperature range. It is also known that potassium formate is soluble in alcohol. One novel feature of the invention is the use of potassium hydroxide and optionally formic acid to isolate and purify the potassium salt or free acid form of the resulting aminocarboxylates by cooling and the use of a water-soluble alcohol.

The disclosed method involves neutralizing an amine with potassium hydroxide and adding a solution of halogenated carboxylic acid selected from chlorinated, brominated, or iodinated carboxylic acids neutralized with potassium hydroxide followed by application of heat and properly maintaining the mixture to a pH of about 10 with potassium hydroxide. The initial combination is at ambient temperature, or between about 20 to 25 degrees C. (about 68 to 77 degrees F.). The combination is heated to between about 90 to 100 degrees C. and maintained at that temperature during the reaction time. Once the pH remains constant without the addition of potassium hydroxide, the reaction mixture is heated for an additional 10 minutes. The resulting solution is then cooled in an ice water bath taking the temperature of the solution down to between about 0 to 10 degrees C. and the resulting potassium salt solid is precipitated and isolated. The filtrate containing the aminocarboxylate potassium salt may be used without further purification, or may optionally be converted to the corresponding acid. Conversion to the corresponding acid involves acidifying the filtrate containing the aminocarboxylate potassium salt with formic acid to approximately pH 3 and mixing it with about twice the volume of alcohol. The biphasic liquid is then chilled to between approximately 0° C. to 10° C., or between approximately 0° C. to 5° C., or between about 0° C. to 2° C. and the lower phase containing the aminocarboxylic acid is separated and collected. The aqueous phase containing the aminocarboxylic acid may optionally be treated with an equal portion of water-soluble alcohol to further remove any residual impurities and increase the concentration of the final product. The lower phase is at least about 30% aminocarboxylic acid concentration, more preferably about 40% by weight.

If the starting amine contains an acid group, the synthesis of the invention begins by neutralizing the acid with potassium hydroxide. In contrast, if the beginning amine does not contain an acid group, the neutralization step with potassium hydroxide is unnecessary. Examples of such acid groups include but are not limited to carboxylates, sulfates, sulfonate, and ionizable alcohols. An example of an amine-functional group not containing an acid group includes but is not limited to monoalkyl amines such as ethyl amine, methyl amine, or propanol amine.

The next step in the synthesis involves reacting a mixture of the amino-functional group-containing molecule with the potassium salt of halogenated carboxylic acid in the presence of potassium hydroxide and heat. Examples of suitable halogenated carboxylic acids include chlorinated, brominated, and iodinated carboxylic acids. In preferred embodiments, the halogenated carboxylic acid is selected from chloroacetic acid, bromoacetic acid, iodoacetic acid, chloropropionic acid, bromopropionic acid, or iodopropionic acid. In a more preferred embodiment, chloroacetic acid is used. The halogenated carboxylates that are not suitable for use in the present invention are fluorinated carboxylic acids as well as astatined carboxylic acids. One skilled in the art will recognize that the strong electronegativity of fluorine will hinder its replacement by nitrogen. Astatine, on the other hand, is radioactive and readily decays.

Heat is preferably used to drive the reaction and may be applied to the container in any conventional manner including but not limited to an electric hot plate, a heating mantle, a steam jacket or a hot bath. The ratio of the potassium salt of an amino-functional group containing a mono substituted amine to the potassium salt of halogenated carboxylic acid is at least 1:2 on a stoichiometric ratio per amino-functional group. The ratio of the potassium salt of an amino-functional group containing a secondary amine to the potassium salt of halogenated carboxylic acid is at least 1:1 on a stoichiometric ratio per amino-functional group. In either case, more halogenated carboxylic acid may be added which may drive the reaction faster and may be possible to complete the reaction without the addition of heat; however, to reduce costs and simplify the purification, the ratio is preferably about 1:2 in the case of primary amines and preferably about 1:1 in the case of secondary amines.

The resultant mixture is then chilled. Again, any method known may be used to chill the mixture including but not limited to placing the container in an ice bath, placing the container in a freezer, using a cooling jacket, by the use of cooling coils, and so on. Cooling the mixture causes the potassium salt to precipitate.

The precipitate is then separated from the mixture. The separation may be accomplished by means of a basket centrifuge or any other method for separation of solids from liquids and saving the liquid phase.

In a preferred embodiment, the liquid phase remains chilled during the purification step to hasten separation and more readily demarcate the resultant biphasic liquid. The chilled temperature in this case is between about 0° C. to 10° C. but preferably closer to 0° C. However, one skilled in the art will recognize that chilling is optional.

To the liquid phase, water-soluble alcohol is added to purify the carboxylated amine potassium salt. Alcohol serves to remove impurities and excess water from the mixture and cause further precipitation of the residual potassium salt. Two liquid phases result. A third, solid phase in the form of a precipitate may also be present. The precipitate is removed by any method of separation of solids and liquids. The liquid is placed into a separatory funnel and the bottom phase is isolated, discarding the upper phase. The remaining lower aqueous phase contains the concentrated potassium salt of the amino carboxylate product, which can be used as such.

The alcohol purification is repeated as many times as preferred in order to maximize the amount of product purified. When referring to alcohol, any water-soluble alcohol may be used to purify the product. Ethanol is a preferred alcohol due to its wide availability and low cost.

Finally, formic acid is optionally added to the alcohol-purified liquid to form the free aminocarboxylic acid and potassium formate.

The present invention will be further illustrated in detail with reference to several inventive examples and comparative examples, which are not intended to limit the scope of the invention.

EXAMPLES

Example 1

Synthesis of Potassium Salt of Aspartic Acid-N,N-Diacetic Acid

This Example demonstrates the synthesis of the potassium salt of Aspartatic Acid N,N-Diacetic Acid.

To 13.31 grams (100 millimols) of aspartic acid, 40 grams of 5 Normal potassium hydroxide (200 millimols) was added and mixed to neutralize. Forty-one grams of potassium hydroxide 5 Normal (205 millimols) were added to 19.37 grams of chloroacetic acid (205 millimols) and mixed to neutralize. The neutralized chloroacetic acid was added to the neutralized aspartic acid and the mixture was heated to boiling.

Twenty-six grams of potassium hydroxide (130 millimols) was added stepwise as needed to maintain a pH of about 10. Once the pH was stable without further addition of potassium hydroxide, the solution was heated for an extra 10 minutes at boiling temperature. The solution was then chilled in an ice bath and 11.91 grams of potassium chloride (185 millimols) precipitated which was separated by filtration and discarded. Approximately 0.97 grams of potassium chloride remained in the solution containing the potassium salt of Aspartic Acid-N,N-Diacetic Acid.

Example 1 demonstrates that a very pure product is formed.

Example 2

Synthesis of Aspartic Acid-N,N-Diacetic Acid

To 13.31 grams of aspartic acid (100 millimols) was added 40 grams of 5 Normal potassium hydroxide (200 millimols) and mixed to dissolve. Fifty grams 5 Normal potassium hydroxide (250 millimols) was added to 23.63 grams chloroacetic acid (250 millimols) and mixed to dissolve. The neutralized chloroacetic acid solution was added to the neutralized aspartic acid solution and the resultant solution was heated to boiling.

Forty grams of potassium hydroxide (200 millimols) was added stepwise throughout the reaction as needed to maintain the pH at about 10. Once the pH was stable without further addition of potassium hydroxide, the solution was boiled for an additional 10 minutes. The solution was then chilled in an ice bath, causing potassium chloride precipitation. The precipitate (14 grams) was filtered and discarded and 25 grams of formic acid was added to the liquid to acidify the solution to a pH of about 4.

To the resulting 80 ml of acidified solution was added 80 ml of ethyl alcohol causing precipitation of 0.62 grams of potassium chloride. The precipitate was again filtered, the lower liquid phase collected (67.7 grams) and a small sample of it was run on an infrared spectrophotometer showing that aspartic acid-N,N-diacetic acid was formed. The product was free of nitrilotriacetic acid as determined by the infrared spectra.

Example 3

Synthesis of Cysteine-N,N-Diacetic Acid

This Example demonstrates the synthesis of Cysteine-N,N-Diacetic Acid.

To 40 grams of a 5 Normal solution of potassium hydroxide, 211 grams of cysteine was added and the combination was stirred to dissolve the cysteine. Separately, 56.7 grams chloroacetic acid was dissolved in 40 grams of 5 Normal solution of potassium hydroxide. The two aforementioned solutions were mixed together. The resulting combined solution was heated to boil and potassium hydroxide was added as needed to maintain the solution at a pH of about 10. Once the pH was stable without further addition of potassium hydroxide, the solution was heated for an additional 5 to 10 minutes. The solution was chilled in an ice bath causing the precipitation of potassium chloride. The precipitated potassium chloride was filtered and discarded. The remaining liquid phase was acidified to pH 3 with formic acid and an equal volume of ethanol was added to the acidified solution. The resulting precipitate was filtered and discarded. A biphasic liquid resulted. The bottom aqueous layer containing the Cysteine-N,N-Diacetic Acid was isolated using a separatory funnel.

Infrared spectrophotometry indicated that Cysteine-N,N-Diacetic Acid was formed. The product was free of nitrilotriacetic acid as determined by the infrared spectra.

Example 4

Synthesis of Methionine-N,N-Diacetic Acid

This Example demonstrates the synthesis of Methionine N,N-Diacetic acid.

The protocol of Example 2 was followed using 29.84 g methionine in 80 ml 5N KOH. The neutralized chloroacetic acid was prepared using 56.7 g chloroacetic acid in 120 ml 5N KOH.

Upon finishing the protocol of Example 2 using the starting materials identified in the previous paragraph, formic acid was added to the supernatant until a pH of 3 was reached. An equal amount of alcohol was added and the precipitate was filtered. The liquid phase of the mix was collected. As compared to the Aspartic Acid-N,N-Diacetic acid, no phase separation was identifiable suggesting the product is very soluble in the water-alcohol mix. For every 100 ml of filtrate, 25 ml of extra ethanol was added and the lower phase was collected resulting in 54.6 g of product obtained. IR Spectrometry was taken on the product to confirm that methionine-N,N-Diacetic acid was synthesized. The product was free of nitrilotriacetic acid as confirmed by the infrared spectra.

Example 5

Testing activity of Methionine N,N-Diacetic Acid

The activity of the Methionine-N,N-Diacetic Acid synthesized in Example 4 above was determined. The product was titrated using 0.25 molar calcium chloride solution as the titrant. The results showed that the product was 26.12% active.

Example 6

Testing Efficacy of Methionine N,N-Diacetic Acid and Aspartic Acid N,N-Diacetic Acid The Methionine-N,N-Diacetic acid prepared in Example 4 above and the Aspartic Acid-N,N-Diacetic Acid prepared in Example 2 above were tested for their usefulness as a chelating agent.

One liter solutions containing sixteen grains of water hardness were prepared using a mix of calcium and magnesium bicarbonate (3:1 ratio) and heated to 85 degrees Fahrenheit. (One grain of hardness is equal to 17.11854 ppm of calcium carbonate).

To each beaker, 3.13 g of a solution of 26.12% active Methionine-N,N-Diacetic Acid as prepared in Example 4 above (stoichiometrically equivalent to 18 grains of hardness) was added. Ten milliliters of a stock solution containing sodium hydroxide and sodium carbonate which upon dilution contained 330 ppm of caustic soda and 300 ppm of sodium carbonate. Transmittance of each of the samples was taken at 85 degrees, 140 degrees, and 160 degrees Fahrenheit, using a Bausch & Lomb Spectronic 20 spectrophotometer, at 550 nm wave length and a 1 centimeter cell path. The results are shown on the table below.

The same experiment was repeated for Aspartic Acid N,N-Diacetic Acid using 1.83 g of a solution 38.03% active prepared in Example 2 above (stoichiometrically equivalent to 16.31 grains of hardness). The results are shown in the table below.

| | Percent transmittance | |
|---|---|---|
| Temperature (Degrees F.) | 16 grain/aspartic | 16 grain/methionine |
| 85 | 100% | 100% |
| 140 | 100% | 100% |
| 160 | 99% | 100% |

A percent transmittance of 100 reflects total transparency. Ninety to ninety-five transmittance is completely transparent to the naked eye. In the particular case of this Example 6, the results show that the tested materials were successful in chelating all the hardness in the water preventing the formation and precipitation of the calcium and magnesium carbonate.

In short, the results demonstrate that the Aspartic Acid-N,N-Diacetic Acid and the Methionine-N,N-Diacetic Acid were successful chelating agents.

Example 7

Synthesis of Diglycolamine-N,N-Diacetic Acid

This Example demonstrates a synthesis procedure that does not require the neutralization of the starting amine molecule because it lacks an acidic group.

Diglycolamine, also known as aminoethoxyethanol, is a primary amine having a molecular weight of 105.05 g/mol. Diglycolamine was used to synthesize the N,N-dicarboxylate potassium salt using the procedure described below.

Forty grams 5 Normal potassium hydroxide was mixed with 18.9 g chloroacetic acid to neutralize the acid. To the mixture, 10.51 g of diglycolamine was slowly added while stirring. During this addition, the mixture was heated to about 100° C. More potassium hydroxide, for a total of 36 grams 5N potassium hydroxide, was added as needed to maintain the pH at about 10. Once the pH was stabilized without further addition of potassium hydroxide, the mixture that was initially at ambient temperature (between about 20 and 25 degrees C.) was heated to between about 90 to 100 degrees C. for about 10 additional minutes or until the reaction was complete.

The solution was then chilled using ice to a temperature of about 0 degrees C. causing a precipitate to form. The potassium chloride precipitate was filtered and 82.83 g of liquid was recuperated. An equal weight of alcohol (82.83 g of ethanol) was added to the filtrate solution and the mixture was chilled to further precipitate potassium chloride. The precipitate was removed and the liquid phase was collected. If separation would occur, the upper layer would be discarded. For this example, two layers did not form; the product was in the alcohol-water layer.

The synthesis was repeated, omitting the alcohol step and the product was used as such. The product was free of NTA as demonstrated by the IR spectrum.

Comparative Example 1

This comparative example demonstrates that using sodium hydroxide to synthesize Aspartic Acid-N,N-Diacetic Acid instead of potassium hydroxide results in an impure product.

13.3 grams of aspartic acid was dissolved in 40 mls of 5N sodium hydroxide. Separately, 28.3 grams of chloroacetic acid was dissolved in 60 ml of 5N sodium hydroxide. Separately, to 60 mls 5 Normal sodium hydroxide was added 28.3 g chloroacetic acid and the combination was mixed to dissolve and neutralize the chloroacetic acid.

The neutralized aspartic acid and the neutralized chloroacetic acid solutions from the previous paragraph were combined, heated to boiling and 40 ml 5 Normal sodium hydroxide was added as needed to maintain the pH at about 10. Once the pH was maintained without further addition of sodium hydroxide, the solution was boiled for an additional 10 minutes. The final solution was chilled in an ice bath and no precipitate was formed.

The solution was acidified to pH 1 using concentrated HCl resulting in the formation of free Aspartic Acid-N,N-Diacetic Acid. 400 ml of ethanol was added to the free Aspartic Acid-N,N-Diacetic Acid solution forming a small amount of precipitate that was filtered out from a single phase solution. The Aspartic Acid-N,N-Diacetic Acid did not precipitate and as a result, it was contaminated with alcohol and a high concentration of sodium chloride.

The precipitate was dissolved in a small amount of hot water, and then the solution was chilled. Ethanol was added to force precipitation and the precipitate was filtered. To the water/ethanol supernatant was added more ethanol to get more precipitate. The precipitate was filtered and kept separate from the first precipitate.

Infrared spectrophotometry was run on each of the samples. Controls of chloroacetic acid and aspartic acid were also run. The samples showed that no Aspartic Acid-N,N-Diacetic Acid had precipitated.

The features and other details of the invention will now be more particularly described and pointed out in the claims. It will be understood that the particular embodiments of the invention are shown by way of illustration and not as limitations of the invention. The principle features of this invention can be employed in various embodiments without departing from the spirit of the invention.

We claim:

1. A method of synthesizing carboxylated amines, comprising:
    (a) reacting a mixture of potassium salt of a primary or secondary amine having at least one amino-functional group and a potassium salt of a halogenated carboxylic acid selected from the group of brominated carboxylic acid, chlorinated carboxylic acid, or iodinated carboxylic acid, in the presence of potassium hydroxide;
    (b) precipitating the halogenated potassium salt and discarding the precipitate;
    (c) isolating the carboxylated amine present in the liquid phase;
    (d) adding formic acid to the liquid phase to achieve a pH of about 3 to 4 and adding alcohol to the liquid phase to form a biphasic liquid having a lower phase containing an aminocarboxylic acid and an upper phase containing potassium formate; and
    (e) separating the lower liquid phase containing the aminocarboxylic acid from the upper liquid phase containing the potassium formate, wherein the aminocarboxylic acid is free of nitrilotriacetic acid and substantially free of contaminating salt byproducts and further wherein the method of synthesizing is accomplished in the absence of hydrochloric acid.

2. The method of claim 1 further comprising heating the mixture in step (a).

3. The method of claim 1 further comprising selecting the halogenated carboxylic acid from the group consisting of bromoacetic acid, iodoacetic acid, chloroacetic acid, bromopropionic acid, iodopropionic acid, and chloropropionic acid.

4. The method of claim 1 further comprising chloroacetic acid as the chlorinated carboxylic acid.

5. The method of claim 1 wherein the ratio of the potassium salt of the primary amine to the potassium salt of halogenated carboxylic acid is at least 1:2 on a stoichiometric ratio per amino-functional group.

6. The method of claim 1 wherein the ratio of the potassium salt of the secondary amine to the potassium salt of halogenated carboxylic acid is at least 1:1 on a stoichiometric ratio per amino-functional group.

7. The method of claim 1 wherein the step of precipitating the potassium salt in step (b) comprises chilling the reaction mixture from step (a).

8. The method of claim 1 wherein the step of isolating the carboxylated amine from the potassium salt comprises adding water-soluble alcohol to the liquid phase.

9. A method of synthesizing carboxylated amines, comprising:
    a. reacting a mixture of potassium salt of a primary or secondary amine having at least one amino functional group and a potassium salt of chloroacetic acid in the presence of potassium hydroxide;
    b. precipitating the potassium chloride and discarding the precipitate;
    (c) isolating the carboxylated amine present in the liquid phase;
    (d) adding formic acid to the liquid phase to achieve a pH of about 3 to 4 and
    adding alcohol to the supernatant to form a biphasic liquid wherein the lower phase contains the carboxylated amine-containing molecule and the upper phase contains potassium formate; and (e) separating the lower liquid phase containing the aminocarboxylic acid from the upper liquid phase containing the potassium formate, wherein the carboxylated amine is free of nitrilotriacetic acid and substantially free of contaminating salt byproducts and further wherein the method of synthesizing as accomplished in the absence of hydrochloric acid.

10. The method of claim 9 further comprising heating the mixture in step (a) to drive the reaction.

11. The method of claim 9 wherein the ratio of the potassium salt of the primary amine or the secondary amine to the potassium salt of chloroacetic acid is at least 1:1 on a stoichiometric ratio per amino-functional.

12. The method of claim 11 wherein the ratio of the potassium salt of an amino-functional group containing molecule to the potassium salt of chloroacetic acid is 1:2 stoichiometric ratio.

13. The method of claim 9 wherein the step of precipitating the potassium salt in step (b) comprises chilling the reaction mixture from step (a).

14. The method of claim 9 wherein the alcohol in step (d) comprises a water soluble alcohol.

\* \* \* \* \*